United States Patent
Kim

(10) Patent No.: US 11,369,649 B1
(45) Date of Patent: Jun. 28, 2022

(54) COMPOSITION FOR PREVENTION OR TREATMENT OF OCULAR DISEASES COMPRISING EXTRACELLULAR VESICLES DERIVED FROM LACTOBACILLUS PARACASEI

(71) Applicant: MD HEALTHCARE INC., Seoul (KR)

(72) Inventor: Yoon-Keun Kim, Paju-Si (KR)

(73) Assignee: MD HEALTHCARE INC., Seoul (KR)

( * ) Notice: Subject to any disclaimer, the term of this patent is extended or adjusted under 35 U.S.C. 154(b) by 0 days.

(21) Appl. No.: 17/586,414

(22) Filed: Jan. 27, 2022

(30) Foreign Application Priority Data

Jun. 3, 2021 (KR) .................. 10-2021-0072078
Oct. 1, 2021 (KR) .................. 10-2021-0130843

(51) Int. Cl.
*A61K 35/747* (2015.01)
*A61P 27/02* (2006.01)
*A23L 33/135* (2016.01)
*A23L 33/00* (2016.01)

(52) U.S. Cl.
CPC .......... *A61K 35/747* (2013.01); *A23L 33/135* (2016.08); *A23L 33/40* (2016.08); *A61P 27/02* (2018.01); *A23V 2002/00* (2013.01); *A23Y 2220/63* (2013.01)

(58) Field of Classification Search
CPC ...................................................... A61P 27/02
See application file for complete search history.

(56) References Cited

U.S. PATENT DOCUMENTS

2020/0206282 A1* 7/2020 Kim .................. A61P 35/00

FOREIGN PATENT DOCUMENTS

WO WO-2019216662 A1 * 11/2019 ........... A23L 33/135

OTHER PUBLICATIONS

Choi, J. et al. "Lactobacillus paracesei—derived extracellular vesicles attenuate the intestinal inflammatory response by augmenting the endoplasmic reticulum stress pathway", Experimental & Molecular Medicine, 2020, 52:423-437.*
Morita, Y. et al. "Lactobacillus paracasei KW3110 prevents blue light-induced inflammation and degeneration in the retina", Nutrients 2018, 10, 1991; doi:10.3390/nu10121991.*

* cited by examiner

*Primary Examiner* — Gina C Justice
(74) *Attorney, Agent, or Firm* — Vorys, Sater, Seymour and Pease LLP; Mih Suhn Koh

(57) ABSTRACT

The claimed subject matter relates to *Lactobacillus paracasei*-derived extracellular vesicles and a use thereof, and more particularly, to a composition for alleviating, preventing and treating an ocular disease, which includes *Lactobacillus paracasei*-derived extracellular vesicles as an active ingredient, capable of effectively inhibiting the occurrence of an ocular disease caused by oxidative stress-mediated cell senescence.

13 Claims, 8 Drawing Sheets

1: brain; 2: lung; 3: liver; 4: stomach; 5: small intestine; 6: large intestine; 7: kidney

COMPOSITION FOR PREVENTION OR TREATMENT OF OCULAR DISEASES COMPRISING EXTRACELLULAR VESICLES DERIVED FROM LACTOBACILLUS PARACASEI

TECHNICAL FIELD

The present invention relates to *Lactobacillus paracasei*-derived extracellular vesicles and a use thereof, and more particularly, to a composition for preventing or treating an ocular disease, which comprises *Lactobacillus paracasei*-derived extracellular vesicles as an active ingredient.

This application claims priority to and the benefit of Korean Patent Application Nos. 10-2021-0072078 and 10-2021-0130843 filed in the Korean Intellectual Property Office on Jun. 3, 2021 and Oct. 1, 2021, respectively, and all the contents disclosed in the specification and drawings of the applications are incorporated in this application.

BACKGROUND ART

Since the beginning of the 21st century, acute infectious diseases recognized as epidemic diseases in the past have become less important, whereas chronic diseases accompanied by immune dysfunction caused by disharmony between humans and microbiomes have changed disease patterns as main diseases that determine the quality of life and human lifespan. As $21^{st}$ century intractable chronic diseases characterized by abnormalities in immune and metabolic functions caused by various stresses, cancer, cardiovascular diseases, chronic lung diseases, metabolic diseases, and neuro-psychiatric diseases are major diseases determining human lifespans and quality of life and becoming a big problem in public health.

Immunity is a cellular defense mechanism against biological, chemical, physical and mental stress, and occurs through innate immunity and adaptive immunity. Metabolism is to make energy required for the body to produce various materials performing cell functions, and provides proteins and lipids, which have been produced in the endoplasmic reticulum (ER) by ATP produced in mitochondria, to a region in need thereof. Cells face various stresses from the moment they are generated, and biological, chemical, physical, and psychiatric stress induces ER stress in cells, and when the ER stress is maintained, the cells die or are converted into cancer cells. Therefore, it has been recently revealed that many intractable diseases, which are currently problematic, are caused by abnormalities in immune and metabolic functions due to repetitive ER stress.

Meanwhile, the retina of the eye is an organ belonging to the central nervous system, and mature retinal cells do not divide under normal conditions like neuronal cells. Accordingly, when the function of retinal cells decreases, it is easy to have abnormalities in visual function, and aging rapidly progresses. The biggest cause of deteriorated retinal cell function is oxidative stress, which is because tissues for constituting the eye, including the retina, optic nerve, photoreceptor cells and lens, are constantly exposed to oxidative stress such as light and UV in daily life. Due to such oxidative stress, as the alteration of DNA, proteins and lipids constituting a cell occurs and cell death is induced, ocular aging occurs, and seriously, age-related ocular diseases such as geographic atrophy, diabetic retinopathy, cataracts, glaucoma and dry eye occur.

In addition, when vision-related cells do not properly defend against environmental stress such as blue light and UV, inflammation of eyes occurs, and chronic inflammatory ocular disease occurs due to repeated stress. Recently, in order to treat or prevent these chronic inflammatory ocular diseases, interest in an inhibitor of an inflammatory cytokine, TNF-α, which is known as a major mediator of an inflammatory disease, is increasing.

It is known that the number of microorganisms that coexist in the human body reaches 100 trillion, which is about 10-fold larger than that of human cells, and the number of genes of microorganisms is 100-fold larger than that of humans. A microbiota or microbiome refers to a microbial community including bacteria, archaea and eukarya present in a given habitat.

Bacteria that coexist in our bodies and bacteria that exist in the surrounding environment secrete nanometer-sized vesicles to exchange information such as genes, low molecular compounds, and proteins with other cells. The mucosa forms a physical defense membrane through which particles having a size of 200 nanometers (nm) or more cannot pass, so that bacteria coexisting in the mucosa cannot pass through the mucosa, but bacteria-derived extracellular vesicles have a size of approximately 20 to 200 nanometers, and thus relatively freely pass through epithelial cells via the mucosa to be absorbed in our bodies. As described above, although bacteria-derived extracellular vesicles are secreted from bacteria, they differ from bacteria in terms of their constituents, absorption rate in the body, and risk of side effects, and therefore, the use of bacteria-derived extracellular vesicles is completely different from that of living cells or has a significant effect.

Locally secreted bacterial-derived extracellular vesicles are absorbed through the epithelial cells of the mucosa to induce a local inflammatory response, and vesicles that have passed through the epithelial cells are systemically absorbed to be distributed to respective organs, and regulate immune and inflammatory responses in the distributed organs. For example, vesicles derived from pathogenic bacteria such as *Escherichia coli* are pathogenic nanoparticles mimicking viruses, causing colitis or food poisoning locally, and when absorbed into a blood vessel, promote systemic inflammatory responses and blood coagulation through a vascular endothelial inflammatory response. On the other hand, vesicles derived from beneficial bacteria may control diseases by regulating abnormalities in immune and metabolic functions caused by pathogenic vesicles.

Lactic acid bacteria include a large number of bacteria converting carbohydrates into lactic acid, and are known to ferment foods such as yogurt, lactic acid bacterial drinks, and kimchi, to protect the body from other pathogenic microbes due to being present in digestive organs (enteric bacteria) such as intestines or in the vagina, and to help maintain homeostasis. Among the lactic acid bacteria, *Lactobacillus paracasei* is aerobic lactic acid bacteria which do not form spores, and is known to serve as symbiotic bacteria in the human gastrointestinal tract and a woman's vagina to protect the human body from pathogenic bacteria.

However, there is no reported case of application of *Lactobacillus paracasei*-derived extracellular vesicles to treat age- or inflammation-related ocular diseases.

DISCLOSURE

Technical Problem

To solve the problems in the conventional art described above, the present invention is directed to providing a pharmaceutical composition for preventing or treating an ocular disease, comprising *Lactobacillus paracasei*-derived extracellular vesicles as an active ingredient.

In addition, another object of the present invention is to provide a food composition for preventing or alleviating an ocular disease, comprising vesicles derived from *Lactobacillus paracasei* as an active ingredient.

In addition, still another object of the present invention is to provide an quasi-drug composition for preventing or treating an ocular disease, comprising vesicles derived from *Lactobacillus paracasei* as an active ingredient.

In addition, still another object of the present invention is to provide an inhalable composition for preventing or treating an ocular disease, comprising vesicles derived from *Lactobacillus paracasei* as an active ingredient.

In addition, still another object of the present invention is to provide a composition for drug delivery for treating a ocular disease, comprising vesicles derived from *Lactobacillus paracasei* as an active ingredient.

However, a technical problem to be achieved by the present invention is not limited to the aforementioned problems, and the other problems that are not mentioned may be clearly understood by a person skilled in the art from the following description.

Technical Solution

The present invention provides a pharmaceutical composition for preventing or treating an ocular disease, comprising vesicles derived from *Lactobacillus paracasei* as an active ingredient.

In addition, the present invention provides a food composition for preventing or alleviating an ocular disease, comprising vesicles derived from *Lactobacillus paracasei* as an active ingredient.

In addition, the present invention provides a quasi-drug composition for preventing or alleviating an ocular disease, comprising vesicles derived from *Lactobacillus paracasei* as an active ingredient.

In addition, the present invention provides an inhalable composition for preventing or alleviating an ocular disease, comprising vesicles derived from *Lactobacillus paracasei* as an active ingredient.

In addition, the present invention provides a composition for drug delivery for treating a ocular disease, comprising vesicles derived from *Lactobacillus paracasei* as an active ingredient.

In one embodiment of the present invention, the ocular disease may be an age-related ocular disease, but the present invention is not limited thereto.

In another embodiment of the present invention, the ocular disease may be inflammatory ocular disease, but the present invention is not limited thereto.

In still another embodiment of the present invention, the ocular disease may be one or more diseases selected from the group consisting of Leber congenital amaurosis (LCA), Stargardt's disease, Usher syndrome, choroidal insufficiency, Rod-Cone or Cone-Rod dystrophy, ciliopathy, a mitochondrial disorder, progressive retinal atrophy, a degenerative retinal disease, age-related macular degeneration (AMD), wet AMD, dry AMD, map atrophy, familial or acquired maculopathy, a retinal photoreceptor disease, a retinal pigment epithelium-related disease, diabetic retinopathy, cystic macular edema, retinal detachment, traumatic retinal damage, iatrogenic retinal damage, a macular hole, macular telangiectasia, a ganglion cell disease, an optic nerve cell disease, glaucoma, a cataract, optic neuropathy, ischemic retinal disease, retinopathy of prematurity, retinal vessel occlusion, familial macroaneurism, a retinal vascular disease, an ophthalmic vascular disease, retinal nerve cell degeneration caused by glaucoma and ischemic optic neuropathy, but the present invention is not limited thereto.

In still another embodiment of the present invention, the inflammatory ocular disease may be one or more diseases selected from the group consisting of retinitis pigmentosa (RP), conjunctivitis, scleritis, keratitis, iritis, uveitis, chorioretinitis, choroiditis, and retinitis, but the present invention is not limited thereto.

In still another embodiment of the present invention, the inflammatory ocular disease may be mediated by IL-6, but the present invention is not limited thereto.

In yet another embodiment of the present invention, the ocular disease may be an ocular disease caused by immune dysfunction or metabolic dysfunction, but the present invention is not limited thereto.

In yet another embodiment of the present invention, the ocular disease may be an ocular disease caused by oxidative stress, but the present invention is not limited thereto.

In yet another embodiment of the present invention, the vesicles may have an average diameter of 10 to 300 nm, but the present invention is not limited thereto.

In yet another embodiment of the present invention, the vesicles may be naturally or artificially secreted from *Lactobacillus paracasei*, but the present invention is not limited thereto.

In yet another embodiment of the present invention, the vesicles may be isolated from a *Lactobacillus paracasei* culture solution or a food prepared by adding *Lactobacillus paracasei*, but the present invention is not limited thereto.

Further, the present invention provides a method for preventing or treating an ocular disease, the method comprising administering a composition comprising vesicles derived from *Lactobacillus paracasei* to a subject.

In addition, the present invention provides a use of a composition comprising vesicles derived from *Lactobacillus paracasei* for preventing or treating an ocular disease.

Further, the present invention provides a use of vesicles derived from *Lactobacillus paracasei* for preparing a drug for preventing or treating an ocular disease.

In addition, the present invention provides a use of vesicles derived from *Lactobacillus paracasei* for preparing a food for preventing or alleviating an ocular disease.

Further, the present invention provides a use of vesicles derived from *Lactobacillus paracasei* for preparing a quasi-drug for preventing or alleviating an ocular disease.

In addition, the present invention provides a method for delivery of drug for treating an ocular disease, the method comprising administering a composition comprising vesicles derived from *Lactobacillus paracasei* to a subject.

Further, the present invention provides a use of a composition comprising vesicles derived from *Lactobacillus paracasei* for delivery of drug for treating an ocular disease.

In addition, the present invention provides use of vesicles derived from *Lactobacillus paracasei* for preparing a drug delivery agent for treating an ocular disease.

Advantageous Effects

It was confirmed that, after being absorbed into the body, *Lactobacillus paracasei*-derived extracellular vesicles according to the present invention are distributed to the central nervous system through the blood brain barrier (BBB), and after being absorbed into cells, effectively inhibit the secretion of IL-6, which is the main mediator of intractable inflammatory diseases, activate AMPK signaling to increase metabolic function, and efficiently inhibit the occurrence of an ocular disease caused by cell senescence and inflammation. Further, as it was confirmed that, when the vesicles were administered into a rabbit model with an ocular disease caused by oxidative stress, the occurrence of retinal degeneration caused by oxidative stress was significantly inhibited, the *Lactobacillus paracasei*-derived extracellular vesicles according to the present invention can be expected to be widely used as a drug for alleviating, preventing or treating an ocular disease.

BEST MODES OF THE INVENTION

Figure 1:
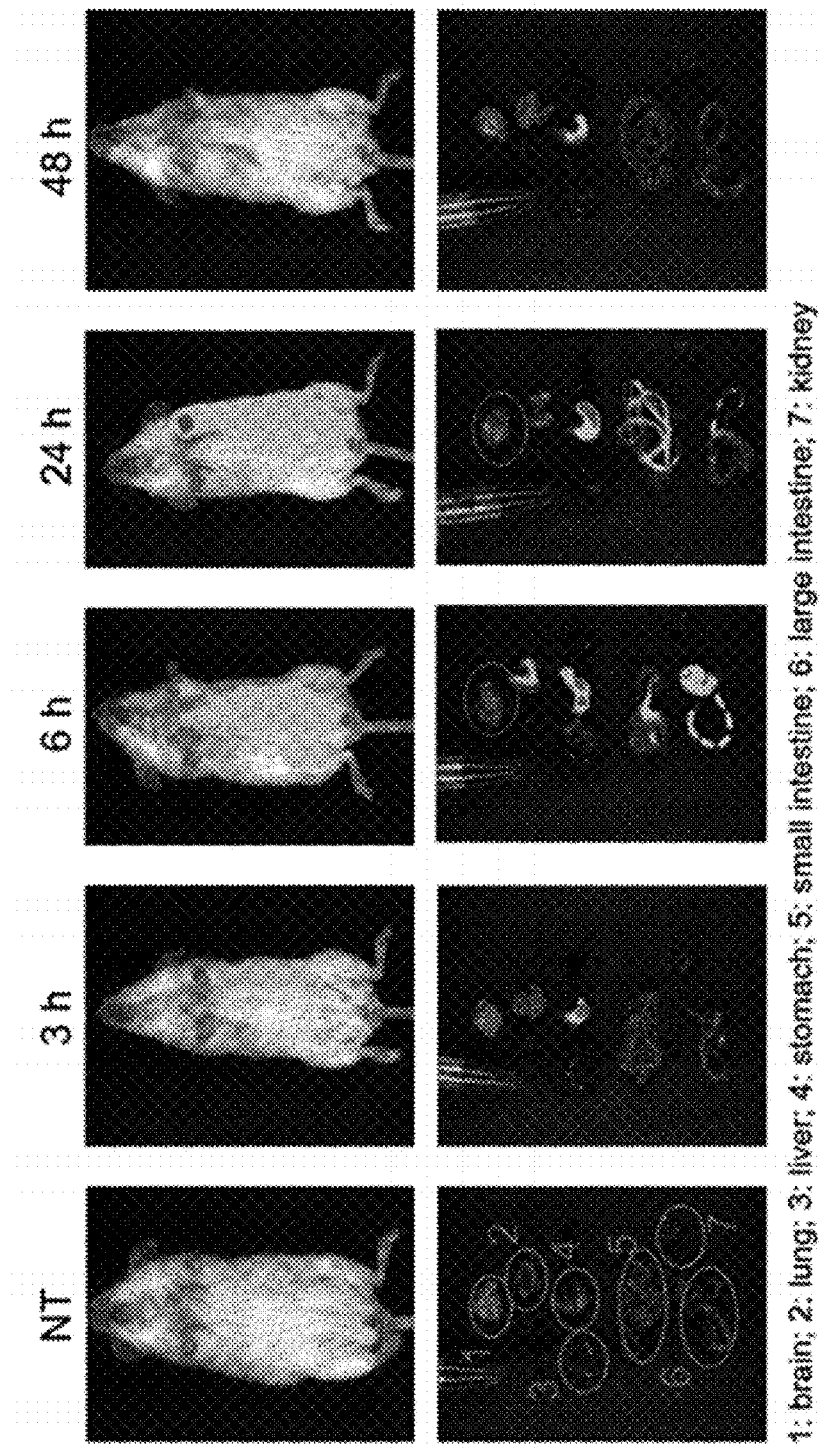
FIG. 1 is a result of analyzing the distribution pattern of *Lactobacillus paracasei*-derived extracellular vesicles after oral administration according to one embodiment of the present invention.

The present invention relates to *Lactobacillus paracasei*-derived extracellular vesicles and a use thereof.

The present inventors isolated the vesicles derived from *Lactobacillus paracasei*.

The inventors confirmed that *Lactobacillus paracasei*-derived extracellular vesicles are well delivered to several organs after oral administration of the vesicles, and are migrated and distributed in the central nervous system including the retina through the blood-brain barrier (BBB) (see Example 2).

In addition, the inventors confirmed that *Lactobacillus paracasei*-derived extracellular vesicles inhibited IL-6 secretion in response to inflammation caused by LPS, and such an inhibitory effect is maintained by heat treatment, acid treatment, and bile treatment on the vesicles (see Example 3).

In addition, the inventors confirmed that, as autophagy is induced by activating AMPK signaling, which is a key signaling factor of regulation of a metabolic disorder, by *Lactobacillus paracasei*-derived extracellular vesicles, an ocular disease caused by a metabolic disorder can be treated by increasing the homeostasis of metabolic function (see Example 4).

In addition, the inventors confirmed that, as a result of oral administration of *Lactobacillus paracasei*-derived extracellular vesicles to a rabbit model with macular degeneration caused by oxidative stress, macular degeneration caused by the degeneration of the retinal pigment epithelial cell layer is significantly reduced (see Example 5).

Thus, the present invention provides a composition for preventing, alleviating, or treating an ocular disease, comprising vesicles derived from *Lactobacillus paracasei* as an active ingredient. The composition includes a pharmaceutical composition, a food composition, and a quasi-drug composition.

Hereinafter, a use of *Lactobacillus paracasei*-derived extracellular vesicles of the present invention for preventing, alleviating or treating an ocular disease will be described in detail.

As used herein, the term vesicle or extracellular vesicle refers to a structure formed of a nano-sized membrane secreted from various bacteria, and includes, for example, an extracellular vesicle derived from gram-negative bacteria such as *E. coli*, which has, an endotoxin (lipopolysaccharide), a toxic protein, and both bacterial DNA and RNA, or an extracellular vesicle derived from gram-positive bacteria such as *micrococcus* bacteria, which have outer membrane vesicles (OMVs), a protein and a nucleic acid as well as components of a bacterial cell wall, such as peptidoglycan and lipoteichoic acid.

In the specification, the vesicle encompasses all structures which are naturally secreted from *Lactobacillus paracasei*, or formed of an artificially produced membrane.

The vesicles may be isolated by heat treatment or autoclaving during *Lactobacillus paracasei* culture, or using one or more methods selected from the group consisting of centrifugation, ultracentrifugation, autoclaving, extrusion, sonication, cell lysis, homogenization, freezing-thawing, electroporation, mechanical degradation, chemical treatment, filtration with a filter, gel filtration chromatography, pre-flow electrophoresis, and capillary electrophoresis of the cell culture. In addition, for isolation, washing for removing impurities, and concentration of the obtained vesicles may be further performed.

The method for isolating vesicles from the culture solution or fermented food of the *Lactobacillus paracasei* of the present invention is not particularly limited as long as the vesicles are included. For example, vesicles may be isolated using a method such as centrifugation, ultra-high speed centrifugation, filtration by a filter, gel filtration chromatography, free-flow electrophoresis, or capillary electrophoresis, and a combination thereof, and further, a process such as washing to remove impurities and concentration of obtained vesicles may be further included.

The term "ocular disease" used herein refers to an eye-related disease.

The term "age-related ocular disease" used herein is a concept that includes not only an ocular disease caused by degradation of biological functions with aging, but also an ocular disease exhibiting similar symptoms to those of a disease mainly occurring in the elderly due to degradation of biological functions faster than an actual age. In the present invention, the age-related ocular disease may include an ocular disease mediated by AMPK and an ocular disease caused by oxidative stress. The age-related ocular disease may comprise, for example, one or more selected from the group consisting of Leber congenital amaurosis (LCA), Stargardt's disease, Usher syndrome, choroidal insufficiency, Rod-Cone or Cone-Rod dystrophy, ciliopathy, a mitochondrial disorder, progressive retinal atrophy, a degenerative retinal disease, age-related macular degeneration (AMD), wet AMD, dry AMD, map atrophy, familial or acquired maculopathy, a retinal photoreceptor disease, a retinal pigment epithelium-related disease, diabetic retinopathy, cystic macular edema, retinal detachment, traumatic retinal damage, iatrogenic retinal damage, a macular hole, macular telangiectasia, a ganglion cell disease, an optic nerve cell disease, glaucoma, a cataract, optic neuropathy, ischemic retinal disease, retinopathy of prematurity, retinal vessel occlusion, familial macroaneurism, a retinal vascular disease, an ophthalmic vascular disease, retinal nerve cell degeneration caused by glaucoma and ischemic optic neuropathy, but the present invention is not limited thereto.

The term "inflammatory ocular disease" used herein is a concept including all ocular diseases caused by inflammation in the eye due to an inflammatory causative factor, and in the present invention, the inflammatory ocular disease may include an ocular disease mediated by IL-6 or an ocular disease caused by oxidative stress. The inflammatory ocular disease may include, for example, retinitis pigmentosa (RP), conjunctivitis, scleritis, keratitis, iritis, uveitis, chorioretinitis, choroiditis, and retinitis, but the present invention is not limited thereto.

The "retinal geographic atrophy" used herein is a disease in which the retina and choriocapillaris atrophy due to calcification of drusen, which are waste accumulating in the retinal pigment epithelium, due to age-related macular degeneration and poor blood supply, and the atrophied area enlarges in a map shape and spreads to the central region, resulting in loss of vision.

The "age-related macular degeneration (AMD)" used herein is a disease accompanied by various changes due to aging in the macula of the retina, which plays a very important role in vision. In the present invention, the age-related macular degeneration may comprise dry (non-exudative) and wet (exudative) types. The "dry AMD" refers to the case in which there is a lesion such as drusen or retinal pigment epithelium atrophy in the retina, and accounts for almost 90% of AMD. The photoreceptor cells in the macula gradually atrophy, vision gradually decreases, and it can develop into a wet form. In the "wet AMD," new choroidal blood vessels grow under the retina, and severe visual damage is likely to occur due to bleeding or exudation from the new blood vessel itself or blood vessel, and blindness may occur due to disc atrophy and severe hemorrhaging within months to years after onset.

The "diabetic retinopathy" used herein is one of the microvascular complications appearing in diabetes, and is caused by functional and morphological changes in capillaries such as increased vascular permeability in the retina due to high blood pressure and the accompanying several biochemical changes, ischemia and neovascularization. In the present invention, the diabetic retinopathy may comprise non-proliferative or proliferative retinopathy, but the present invention is not limited thereto. The "non-proliferative retinopathy" refers to a condition in which small blood vessels in the retina are weakened and the supply of nutrients is interrupted due to serum leakage or blockage of blood vessels. The "proliferative retinopathy" is known to cause blindness within 5 years due to bleeding from a new blood vessel without suitable treatment for neovascularization in a place with poor blood circulation.

In the present invention, the vesicles may have the form of a spherical shape, and have an average diameter 10-300 nm, 10-200 nm, 10-190 nm, 10-180 nm, 10-170 nm, 10-160 nm, 10-150 nm, 10-140 nm, 10-130 nm, 10-120 nm, 10-110 nm, 10-100 nm, 10-90 nm, 10-80 nm, 10-70 nm, 10-60 nm, 10-50 nm, 20-200 nm, 20-180 nm, 20-160 nm, 20 to 140 nm, 20 to 120 nm, 20 to 100 nm, or 20 to 80 nm, preferably 20-200 nm, but is not limited thereto.

The term "comprising as an active ingredient" used herein refers to a sufficient amount for achieving the efficacy or activity of *Lactobacillus paracasei*-derived extracellular vesicles.

The amount of the vesicles in the composition of the present invention may be appropriately adjusted depending on the symptoms of a disease, the degree of progression of symptoms, the condition of a patient, and the like, and may range from, for example, 0.0001 wt % to 99.9 wt % or 0.001 wt % to 50 wt % with respect to a total weight of the composition, but the present invention is not limited thereto. The amount ratio is a value based on the amount of dried product from which a solvent is removed.

The pharmaceutical composition according to the present invention may further include a suitable carrier, excipient, and diluent which are commonly used in the preparation of pharmaceutical compositions. The excipient may be, for example, one or more selected from the group consisting of a diluent, a binder, a disintegrant, a lubricant, an adsorbent, a humectant, a film-coating material, and a controlled release additive.

The pharmaceutical composition according to the present invention may be used by being formulated, according to commonly used methods, into a form such as powders, granules, sustained-release-type granules, enteric granules, liquids, eye drops, elixirs, emulsions, suspensions, spirits, troches, aromatic water, lemonades, tablets, sustained-release-type tablets, enteric tablets, sublingual tablets, hard capsules, soft capsules, sustained-release-type capsules, enteric capsules, pills, tinctures, soft extracts, dry extracts, fluid extracts, injections, capsules, perfusates, or a preparation for external use, such as plasters, lotions, pastes, sprays, inhalants, patches, sterile injectable solutions, or aerosols. The preparation for external use may have a formulation such as creams, gels, patches, sprays, ointments, plasters, lotions, liniments, pastes, or cataplasmas.

As the carrier, the excipient, and the diluent that may be included in the pharmaceutical composition according to the present invention, lactose, dextrose, sucrose, oligosaccharides, sorbitol, mannitol, xylitol, erythritol, maltitol, starch, acacia rubber, alginate, gelatin, calcium phosphate, calcium silicate, cellulose, methyl cellulose, microcrystalline cellulose, polyvinylpyrrolidone, water, methyl hydroxybenzoate, propyl hydroxybenzoate, talc, magnesium stearate, and mineral oil may be used.

For formulation, commonly used diluents or excipients such as fillers, thickeners, binders, wetting agents, disintegrants, and surfactants are used.

As additives of tablets, powders, granules, capsules, pills, and troches according to the present invention, excipients such as corn starch, potato starch, wheat starch, lactose, white sugar, glucose, fructose, D-mannitol, precipitated calcium carbonate, synthetic aluminum silicate, dibasic calcium phosphate, calcium sulfate, sodium chloride, sodium hydrogen carbonate, purified lanolin, microcrystalline cellulose, dextrin, sodium alginate, methyl cellulose, sodium carboxymethylcellulose, kaolin, urea, colloidal silica gel, hydroxypropyl starch, hydroxypropyl methylcellulose (HPMC) 1928, HPMC 2208, HPMC 2906, HPMC 2910, propylene glycol, casein, calcium lactate, and Primojel®; and binders such as gelatin, Arabic gum, ethanol, agar powder, cellulose acetate phthalate, carboxymethylcellulose, calcium carboxymethylcellulose, glucose, purified water, sodium caseinate, glycerin, stearic acid, sodium carboxymethylcellulose, sodium methylcellulose, methylcellulose, microcrystalline cellulose, dextrin, hydroxycellulose, hydroxypropyl starch, hydroxymethylcellulose, purified shellac, starch, hydroxypropyl cellulose, hydroxypropyl methylcellulose, polyvinyl alcohol, and polyvinylpyrrolidone may be used, and disintegrants such as hydroxypropyl methylcellulose, corn starch, agar powder, methylcellulose, bentonite, hydroxypropyl starch, sodium carboxymethylcellulose, sodium alginate, calcium carboxymethylcellulose, calcium citrate, sodium lauryl sulfate, silicic anhydride, 1-hydroxypropylcellulose, dextran, ion-exchange resin, polyvinyl acetate, formaldehyde-treated casein and gelatin, alginic acid, amylose, guar gum, sodium bicarbonate, polyvinylpyrrolidone, calcium phosphate, gelled starch, Arabic gum, amylopectin, pectin, sodium polyphosphate, ethyl cellulose, white sugar, magnesium aluminum silicate, a di-sorbitol solution, and light anhydrous silicic acid; and lubricants such as calcium stearate, magnesium stearate, stearic acid, hydrogenated vegetable oil, talc, lycopodium powder, kaolin, Vaseline, sodium stearate, cacao butter, sodium salicylate, magnesium salicylate, polyethylene glycol (PEG) 4000, PEG 6000, liquid paraffin, hydrogenated soybean oil (Lubri wax), aluminum stearate, zinc stearate, sodium lauryl sulfate, magnesium oxide, Macrogol, synthetic aluminum silicate, silicic anhydride, higher fatty acids, higher alcohols, silicone oil, paraffin oil, polyethylene glycol fatty acid ether, starch, sodium chloride, sodium acetate, sodium oleate, dl-leucine, and light anhydrous silicic acid may be used.

As additives of liquids according to the present invention, water, dilute hydrochloric acid, dilute sulfuric acid, sodium citrate, monostearic acid sucrose, polyoxyethylene sorbitol fatty acid esters (twin esters), polyoxyethylene monoalkyl ethers, lanolin ethers, lanolin esters, acetic acid, hydrochloric acid, ammonia water, ammonium carbonate, potassium hydroxide, sodium hydroxide, prolamine, polyvinylpyrrolidone, ethylcellulose, and sodium carboxymethylcellulose may be used.

In syrups according to the present invention, a white sugar solution, other sugars or sweeteners, and the like may be used, and as necessary, a fragrance, a colorant, a preservative, a stabilizer, a suspending agent, an emulsifier, a viscous agent, or the like may be used.

In emulsions according to the present invention, purified water may be used, and as necessary, an emulsifier, a preservative, a stabilizer, a fragrance, or the like may be used.

In suspensions according to the present invention, suspending agents such as acacia, tragacanth, methylcellulose, carboxymethylcellulose, sodium carboxymethylcellulose, microcrystalline cellulose, sodium alginate, hydroxypropyl methylcellulose (HPMC) 1828, HPMC 2906, HPMC 2910, and the like may be used, and as necessary, a surfactant, a preservative, a stabilizer, a colorant, and a fragrance may be used.

Injections according to the present invention may include: solvents such as distilled water for injection, a 0.9% sodium chloride solution, Ringer's solution, a dextrose solution, a dextrose+sodium chloride solution, PEG, lactated Ringer's solution, ethanol, propylene glycol, non-volatile oil-sesame oil, cottonseed oil, peanut oil, soybean oil, corn oil, ethyl oleate, isopropyl myristate, and benzene benzoate; cosolvents such as sodium benzoate, sodium salicylate, sodium acetate, urea, urethane, monoethylacetamide, butazolidine, propylene glycol, the Tween series, amide nicotinate, hexamine, and dimethylacetamide; buffers such as weak acids and salts thereof (acetic acid and sodium acetate), weak bases and salts thereof (ammonia and ammonium acetate), organic compounds, proteins, albumin, peptone, and gums; isotonic agents such as sodium chloride; stabilizers such as sodium bisulfite ($NaHSO_3$) carbon dioxide gas, sodium metabisulfite ($Na_2S_2O_5$), sodium sulfite ($Na_2SO_3$), nitrogen gas ($N_2$), and ethylenediamine tetraacetic acid; sulfating agents such as 0.1% sodium bisulfide, sodium formaldehyde sulfoxylate, thiourea, disodium ethylenediaminetetraacetate, and acetone sodium bisulfite; a pain relief agent such as benzyl alcohol, chlorobutanol, procaine hydrochloride, glucose, and calcium gluconate; and suspending agents such as sodium CMC, sodium alginate, Tween 80, and aluminum monostearate.

In suppositories according to the present invention, bases such as cacao butter, lanolin, Witepsol, polyethylene glycol, glycerogelatin, methylcellulose, carboxymethylcellulose, a mixture of stearic acid and oleic acid, Subanal, cottonseed oil, peanut oil, palm oil, cacao butter+cholesterol, lecithin, lanette wax, glycerol monostearate, Tween or span, imhausen, monolan(propylene glycol monostearate), glycerin, Adeps solidus, buytyrum Tego-G, cebes Pharma 16, hexalide base 95, cotomar, Hydrokote SP, S-70-XXA, S-70-XX75(S-70-XX95), Hydrokote 25, Hydrokote 711, idropostal, massa estrarium (A, AS, B, C, D, E, I, T), masa-MF, masupol, masupol-15, neosuppostal-N, paramount-B, supposiro OSI, OSIX, A, B, C, D, H, L, suppository base IV types AB, B, A, BC, BBG, E, BGF, C, D, 299, suppostal N, Es, Wecoby W, R, S, M, Fs, and tegester triglyceride matter (TG-95, MA, 57) may be used.

Solid preparations for oral administration include tablets, pills, powders, granules, capsules, and the like, and such solid preparations are formulated by mixing the composition with at least one excipient, e.g., starch, calcium carbonate, sucrose, lactose, gelatin, and the like. In addition to simple excipients, lubricants such as magnesium stearate and talc are also used.

Examples of liquid preparations for oral administration include suspensions, liquids for internal use, emulsions, syrups, and the like, and these liquid preparations may include, in addition to simple commonly used diluents, such as water and liquid paraffin, various types of excipients, for example, a wetting agent, a sweetener, a fragrance, a preservative, and the like. Preparations for parenteral administration include an aqueous sterile solution, a non-aqueous solvent, a suspension, an emulsion, a freeze-dried preparation, and a suppository. Non-limiting examples of the non-aqueous solvent and the suspension include propylene glycol, polyethylene glycol, a vegetable oil such as olive oil, and an injectable ester such as ethyl oleate.

The pharmaceutical composition according to the present invention is administered in a pharmaceutically effective amount. In the present invention, "the pharmaceutically effective amount" refers to an amount sufficient to treat diseases at a reasonable benefit/risk ratio applicable to medical treatment, and an effective dosage level may be determined according to factors including types of diseases of patients, the severity of disease, the activity of drugs, sensitivity to drugs, administration time, administration route, excretion rate, treatment period, and simultaneously used drugs, and factors well known in other medical fields.

The composition according to the present invention may be administered as an individual therapeutic agent or in combination with other therapeutic agents, may be administered sequentially or simultaneously with therapeutic agents in the related art, and may be administered in a single dose or multiple doses. It is important to administer the composition in a minimum amount that can obtain the maximum effect without any side effects, in consideration of all the aforementioned factors, and this may be easily determined by those of ordinary skill in the art.

The pharmaceutical composition of the present invention may be administered to an a subject via various routes. All administration methods can be predicted, and the pharmaceutical composition may be administered via, for example, oral administration, subcutaneous injection, intraperitoneal administration, intravenous injection, intramuscular injection, intrathecal (space around the spinal cord) injection, sublingual administration, administration via the buccal mucosa, intrarectal insertion, intravaginal insertion, ocular administration, intra-aural administration, intranasal administration, inhalation, spraying via the mouth or nose, transdermal administration, percutaneous administration, or the like.

In the present invention, the ocular administration may be one selected from the group consisting of intraconjunctival administration, intravitreal administration, subretinal administration, suprachoroidal administration, subconjunctival administration and sub-tenon administration, but the present invention is not limited thereto.

The pharmaceutical composition of the present invention is determined depending on the type of a drug, which is an active ingredient, along with various related factors such as a disease to be treated, administration route, the age, gender, and body weight of a patient, and the severity of diseases. Specifically, the effective amount of the composition according to the present invention may vary depending on the patient's age, sex, and body weight, and generally, 0.001 to 150 mg of the composition and preferably, 0.01 to 100 mg of the composition, per 1 kg of the body weight, may be administered daily or every other day or may be administered once to three times a day. However, since the effective amount may be increased or decreased depending on the administration route, the severity of obesity, gender, body weight, age, and the like, the dosage is not intended to limit the scope of the present invention in any way.

As used herein, the "subject" refers to a subject in need of treatment of a disease, and more specifically, refers to a mammal such as a human or a non-human primate, a mouse, a rat, a dog, a cat, a horse, and a cow, but the present invention is not limited thereto.

As used herein, the "administration" refers to providing a subject with a predetermined composition of the present invention by using an arbitrary appropriate method.

The term "prevention" as used herein means all actions that inhibit or delay the onset of a target disease. The term "treatment" as used herein means all actions that alleviate or beneficially change a target disease and abnormal metabolic symptoms caused thereby via administration of the pharmaceutical composition according to the present invention. The term "improvement" as used herein means all actions that reduce the degree of parameters related to a target disease, e.g., symptoms via administration of the composition according to the present invention.

In addition, the present invention provides a food composition comprising vesicles derived from *Lactobacillus paracasei* as an active ingredient.

The food composition may be a health functional food composition, but is not limited thereto.

The vesicles according to the present invention may be used by adding an active ingredient as is to food or may be used together with other foods or food ingredients, but may be appropriately used according to a typical method. The mixed amount of the active ingredient may be suitably determined depending on the purpose of use thereof (for prevention or alleviation). In general, when a food or beverage is prepared, the composition of the present invention is added in an amount of 15 wt % or less, preferably 10 wt % or less based on the raw materials. However, for long-term intake for the purpose of health and hygiene or for the purpose of health control, the amount may be less than the above-mentioned range, and the vesicles have no problem in terms of stability, so the active ingredient may be used in an amount more than the above-mentioned range.

The type of food is not particularly limited. Examples of food to which the material may be added include meats, sausage, bread, chocolate, candies, snacks, confectioneries, pizza, instant noodles, other noodles, gums, dairy products including ice creams, various soups, beverages, tea, drinks, alcoholic beverages, vitamin complexes, and the like, and include all health functional foods in a typical sense.

The health beverage composition according to the present invention may contain various flavors or natural carbohydrates, and the like as additional ingredients as in a typical beverage. The above-described natural carbohydrates may be monosaccharides such as glucose and fructose, disaccharides such as maltose and sucrose, polysaccharides such as dextrin and cyclodextrin, and sugar alcohols such as xylitol, sorbitol, and erythritol. As a sweetener, it is possible to use a natural sweetener such as thaumatin and *stevia* extract, a synthetic sweetener such as saccharin and aspartame, and the like. The proportion of the natural carbohydrates is generally about 0.01 to 0.20 g, or about 0.04 to 0.10 g per 100 ml of the composition of the present invention.

In addition to the aforementioned ingredients, the composition of the present invention may contain various nutrients, vitamins, electrolytes, flavors, colorants, pectic acids and salts thereof, alginic acid and salts thereof, organic acids, protective colloid thickeners, pH adjusters, stabilizers, preservatives, glycerin, alcohols, carbonating agents used in carbonated drinks, and the like. In addition, the composition of the present invention may contain flesh for preparing natural fruit juice, fruit juice drinks, and vegetable drinks. These ingredients may be used either alone or in combinations thereof. The proportion of these additives is not significantly important, but is generally selected within a range of 0.01 to 0.20 part by weight per 100 parts by weight of the composition of the present invention.

Further, the present invention may be provided in the form of an inhalable composition comprising *Lactobacillus paracasei*-derived vesicles as an active ingredient.

In the case of a preparation for inhalation, the compound may be formulated according to a method known in the art, and may be conveniently delivered in the form of an aerosol spray from a pressurized pack or a nebulizer by using a suitable propellant, for example, dichlorofluoromethane, trichlorofluoromethane, dichlorotetrafluoroethane, carbon dioxide, or other suitable gases. In the case of the pressurized aerosol, a dosage unit may be determined by providing a valve for transferring a metered amount. For example, a gelatin capsule and a cartridge for use in an inhaler or insufflator may be formulated so as to contain a powder mixture of a compound and a suitable powder base such as lactose or starch.

In addition, the present invention may provide a quasi-drug composition comprising *Lactobacillus paracasei*-derived extracellular vesicles as an active ingredient.

The term "quasi-drug" used herein means products exhibiting a milder action than pharmaceuticals among products used for diagnosing, curing, improving, alleviating, treating or preventing a human or animal disease. For example, according to the Pharmaceutical Affairs Act, the quasi-drugs exclude products used as pharmaceuticals, and include textile•rubber products used for treating or preventing human•animal diseases, products which act weakly or do not act directly on the human body, and are not instruments or machines or similar thereto, and sterilizers and insecticides for preventing infectious diseases.

In the present invention, the quasi-drug composition may be formulated as an ophthalmic composition, for example, one or more selected from the group consisting of ophthalmic liquids, eye drops, eye ointments, injection solutions, and eyewashes, but the present invention is not limited thereto.

In addition, the present invention provides a composition for delivering a drug for treating an ocular disease, which comprises *Lactobacillus paracasei*-derived extracellular vesicles as an active ingredient.

The term "drug delivery" used herein means any means or act of loading and delivering a drug to the composition according to the present invention in order to deliver a drug to a specific organ, tissue, cell or cell organelle.

MODES OF THE INVENTION

Hereinafter, preferred Examples for helping the understanding of the present invention will be suggested. However, the following Examples are provided only to more easily understand the present invention, and the contents of the present invention are not limited by the following Examples.

EXAMPLES

Example 1: Isolation of Vesicles Derived from *Lactobacillus paracasei*

To isolate *Lactobacillus paracasei*-derived extracellular vesicles (EVs), various *Lactobacillus paracasei* were inoculated into a self-made medium, cultured at 37° C. and 200 rpm until the absorbance ($OD_{600\ nm}$) became 1.0 to 1.5, followed by re-inoculation in the medium and culturing. Then, a supernatant from which bacterial cells had been removed was obtained by recovering the culture solution including bacterial cells and performing centrifugation at 4° C. and 10,000 g for 20 minutes. The obtained supernatant was again filtered using a 0.22 μm filter, and the filtered supernatant was concentrated to a volume of 50 mL or less using a 100 kDa Pellicon 2 Cassette filter membrane (Merck Millipore) and a MasterFlex pump system (Cole-Parmer). A vesicle derived from *Lactobacillus paracasei* (MDH-001) was isolated by filtering the concentrated supernatant again using a 0.22 μm filter. The amount of protein included in the supernatant was measured using the Pierce BCA Protein Assay kit (Thermo Fisher Scientific). The following experiments for the isolated vesicles were conducted.

Example 2. Evaluation of Pharmacokinetic Characteristics of Vesicles Derived from *Lactobacillus paracasei* Bacteria In order to investigate the pharmacokinetic characteristics of *Lactobacillus paracasei*-derived vesicles during oral administration, the fluorescence expressed in the body and each organ from immediately before administration to 72 hours after administration was measured by orally administering vesicles stained with a fluorescent staining reagent Cy7-NHS to mice.

As shown in FIG. 1, the *Lactobacillus paracasei*-derived extracellular vesicles stained with fluorescence were orally administered, and after 1 hour, a fluorescent signal was observed. It can be confirmed that, at 3 hours, weak signal levels were recorded in the stomach, small intestine, large intestine and lungs, and at 6 hours, signals are shown in the brain as well as the stomach, small intestine, large intestine and lungs. Such fluorescence signals showed the strongest signals between 6 and 24 hours after oral administration, and showed a tendency to gradually decrease, and almost disappeared after 48 hours.

Figure 2:
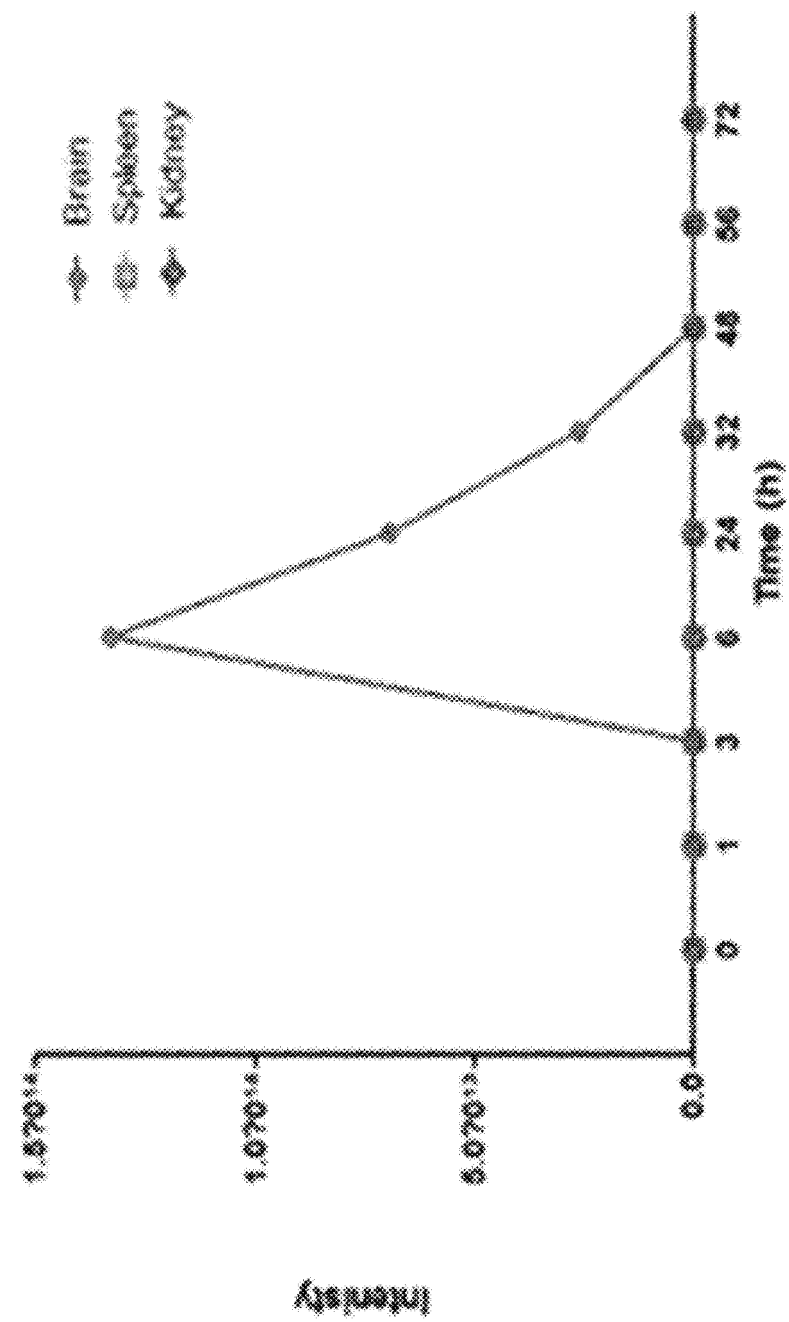
FIG. 2 is a result of analyzing the distribution pattern of *Lactobacillus paracasei*-derived extracellular vesicles in the central nervous system after oral administration according to one embodiment of the present invention.

In addition, as shown in FIG. 2, it was observed that, when the *Lactobacillus paracasei*-derived extracellular vesicles are orally administered, and then a distribution pattern in the central nervous system was evaluated, they were distributed in the central nervous system 3 hours after oral administration, showed a peak at 6 hours, and the signals disappeared after 48 hours.

From the result, it can be seen that, when orally administered, the *Lactobacillus paracasei*-derived extracellular vesicles were absorbed into the body through a mucous membrane, and distributed in various organs, and particularly, they migrated to the central nervous system including the retina through the BBB and distributed.

Example 3: Evaluation of Anti-Inflammatory Effect of *Lactobacillus paracasei*-Derived Extracellular Vesicles on Inflammatory Reaction Caused by LPS To confirm the anti-inflammatory effect of the *Lactobacillus paracasei*-derived extracellular vesicles, mouse macrophages (RAW 264.7 cells) were pre-treated with the *Lactobacillus paracasei*-derived extracellular vesicles at 10 μg/mL or 100 μg/mL, and treated with 100 ng/mL of LPS, which is an inflammation inducer, followed by measuring a secretion amount of IL-6, which is an inflammation-related marker. In addition, to evaluate whether the *Lactobacillus paracasei*-derived extracellular vesicles can be orally administered, heat treatment, acid treatment and bile treatment were performed on the vesicles, and then the secretion amount of IL-6 was measured.

Figure 3:
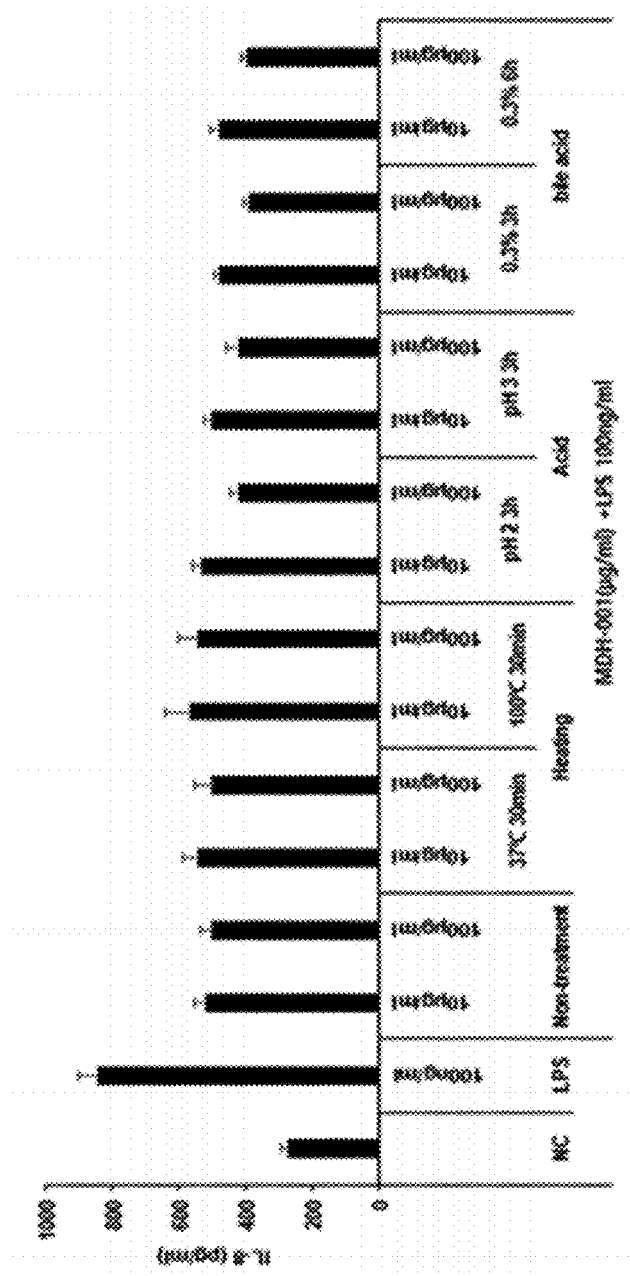
FIG. 3 is a graph evaluating the inhibitory effect of *Lactobacillus paracasei*-derived extracellular vesicles on the influence of inflammatory cytokine secretion by LPS according to one embodiment of the present invention and the therapeutic effect of the vesicles in heat treatment, acid treatment or bile treatment of the *Lactobacillus paracasei*-derived extracellular vesicles (MDH-001: *Lactobacillus paracasei* EVs).

As a result, as shown in FIG. 3, compared to a positive control, which is a group treated with LPS 100 ng/ml of LPS, it was confirmed that the *Lactobacillus paracasei*- derived extracellular vesicles significantly reduce the secretion amount of IL-6. In addition, it was confirmed that, in the heat treatment, acid treatment and bile treatment of the *Lactobacillus paracasei*-derived extracellular vesicles, the effect of inhibiting IL-6 secretion from macrophages was also maintained.

The above results show that the *Lactobacillus paracasei*-derived extracellular vesicles are stable against heat or an acid, and when the vesicles are orally administered, an anti-inflammatory effect can be maintained.

Example 4: Evaluation of Effect of *Lactobacillus paracasei*-Derived Extracellular Vesicles on Activation of AMPK Signaling, which is Key Signaling that Regulates Metabolic Disorder AMP-activated protein kinase (AMPK) signaling inhibits a metabolic disorder occurring in energy depletion through a mechanism such as autophagy. In the present invention, cells were treated with *Lactobacillus paracasei*-derived extracellular vesicles (MDH-001-CM) to evaluate an effect on AMPK activation. DMEM serum-free media into which $2 \times 10^6$ of the cells were seeded were put into a 60-mm cell culture petri dish and cultured for 2 hours. Afterward, the *Lactobacillus paracasei*-derived extracellular vesicles were treated at 0, 0.1, 1 or 10 µg/mL for 1 hour, and were treated with insulin (1 µM) and metformin (50 mM) for 1 hour as comparative groups. To perform a cell lysis assay, a sample-treated petri dish was placed on ice, a supernatant was suctioned, and 5 mL each of a cold PBS buffer was added for washing twice. 10 µL of a protease/phosphatase inhibitor was added to 1 mL of a lysis buffer and well mixed, and 100 µL of a cell lysis buffer was dropped on each dish, and incubated on ice for 5 minutes. After being detached with a scraper, the cells were transferred to a 1.5 mL microtube, and then vortexing and incubation on ice were repeated for 1 minute each for 20 minutes. Afterward, centrifugation was performed at 14,000 rpm for 10 minutes at 4° C., 5 µL and 70 µL of the lysed sample supernatant was transferred to two 1.5-mL microtubes, respectively. The microtube to which 5 µL of the supernatant was transferred was stored at −20° C., and 16.5 µL of 5× sample buffer was put into the microtube to which 70 µL of the supernatant was transferred and boiled at 100° C. for 5 minutes. The boiled sample was stored at −20° C. To perform a BCA quantification analysis, the 1.5-mL microtube to which 5 µL of the lysed sample supernatant was added was taken out at room temperature, vortexed with 20 µL of sterile distilled water, and then spun down. 2, 1, 0.5, 0.25, 0.125, 0.0625, 0.03125 and 0 mg/mL of stocks were prepared by dissolving 2 mg/mL bovine serum albumin (BSA) in sterile distilled water and then diluting by ½. Each concentration of BSA was added at 25 µL into 3 wells in a 96 well polystyrene plate, and 25 µL of the lysed sample was also added to one well. 8 mL of BCA Protein Assay Reagent A and 160 µL of BCA Protein Assay Reagent B were mixed, and then 200 µL thereof was put into the wells. After a reaction in a 37° C. incubator for 30 minutes, absorbance was measured at 562 nm using a SpectraMax M3 microplate reader (Molecular Devices, USA). For western blotting, a 10% gel was prepared during Tris-glycine SDS-polyacrylamide gel electrophoresis, 50 µg of a protein per sample was measured and loaded. After transfer to a nitrocellulose membrane, the reaction was blocked with 5% skim milk, and AMPKα antibodies were diluted 1:400, phospho-AMPKα antibodies were diluted 1:400, and β-actin antibodies were diluted 1:1,000 with 5% skim milk, and mixed overnight with the membrane. After the resulting membrane was washed with a 1×PBST (0.05% Tween-20-containing PBS) solution three times for 5 minutes, anti-rabbit IgG and HRP-linked antibodies were diluted 1:1,000, and mixed with the membrane for 1 hour. The resulting membrane was washed with a 1×PBST solution three times for 5 minutes, and then a solution in which solution A and solution B of the West-Q Chemiluminescent Substrate Kit were mixed at 1:1 was sufficiently sprayed on the membrane, followed by detecting bands using a Chemi-doc system.

Figure 4:
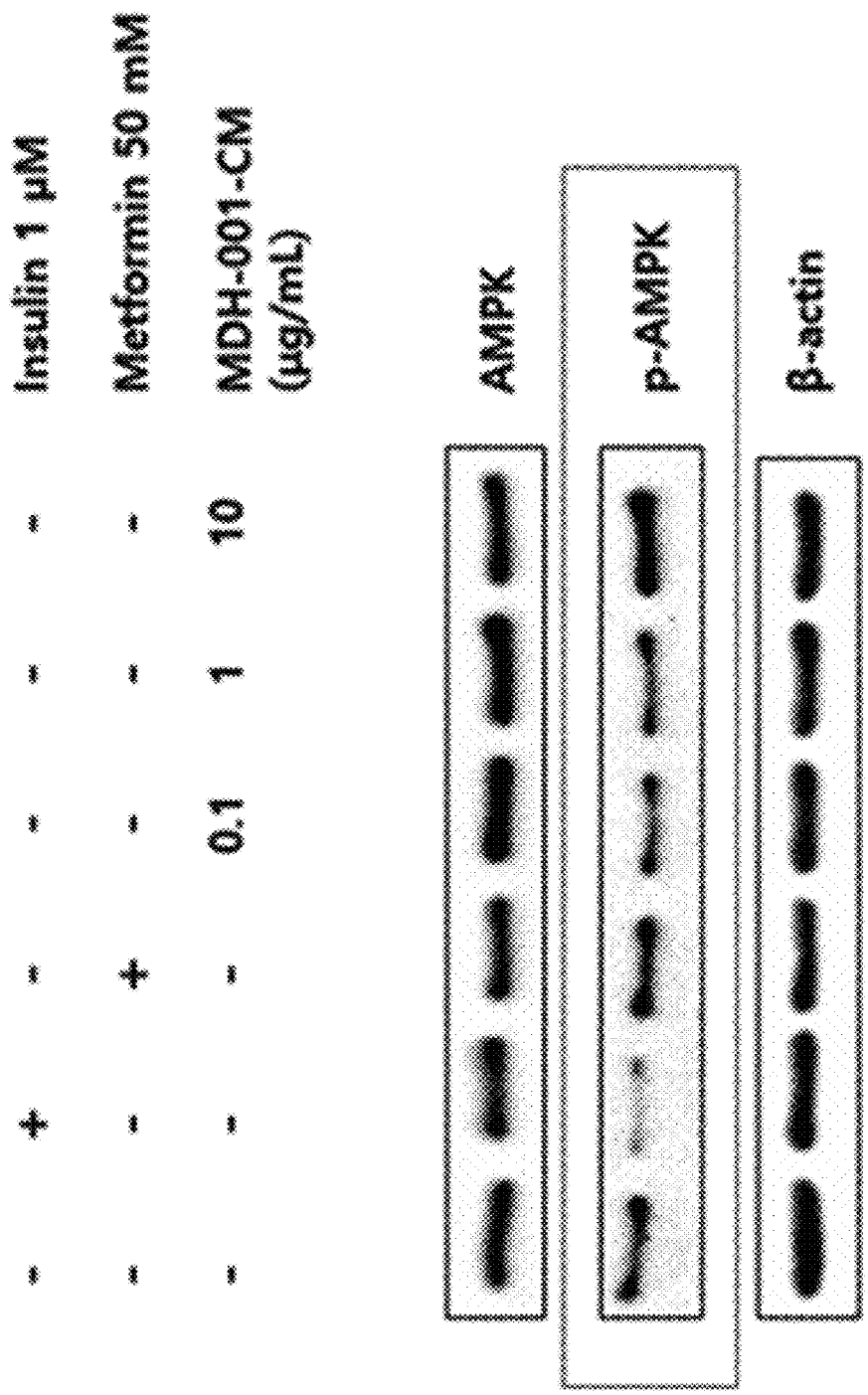
FIG. 4 shows a result of assessing the therapeutic efficacy of *Lactobacillus paracasei*-derived extracellular vesicles on a metabolic function disorder according to one embodiment of the present invention, and evaluating the effect on AMPK signaling which is the key signaling pathway of metabolic function by treatment of cells with metformin as a control drug and *Lactobacillus paracasei*-derived extracellular vesicles (MDH-001: *Lactobacillus paracasei* EVs).

As a result, as shown in FIG. 4, it was confirmed that the expression of phosphorylated AMPK increases depending on a treatment concentration of the *Lactobacillus paracasei*-derived extracellular vesicles (MDH-001-CM). It can be seen that the *Lactobacillus paracasei*-derived extracellular vesicles activate AMPK signaling in a dose-dependent manner, induce autophagy and inhibit a metabolic function disorder, thereby increasing cell homeostasis.

Example 5: Evaluation of Therapeutic Effect of *Lactobacillus paracasei*-Derived Extracellular Vesicles in Rabbit Model with Optical Disease Caused by Oxidative Stress It is known that oxidative stress plays an important role in various ocular diseases such as age-related degeneration (AMD), retinopathy of prematurity, retinal light damage, glaucoma and cataracts in pathological aspects (Beatty S., Koh H., Phil M., Henson D., and Boulton M., "The role of oxidative stress in the pathogenesis of age-related macular degeneration", Surv. Ophthalmol., 45(2): 115-134(2000)).

Figure 5:
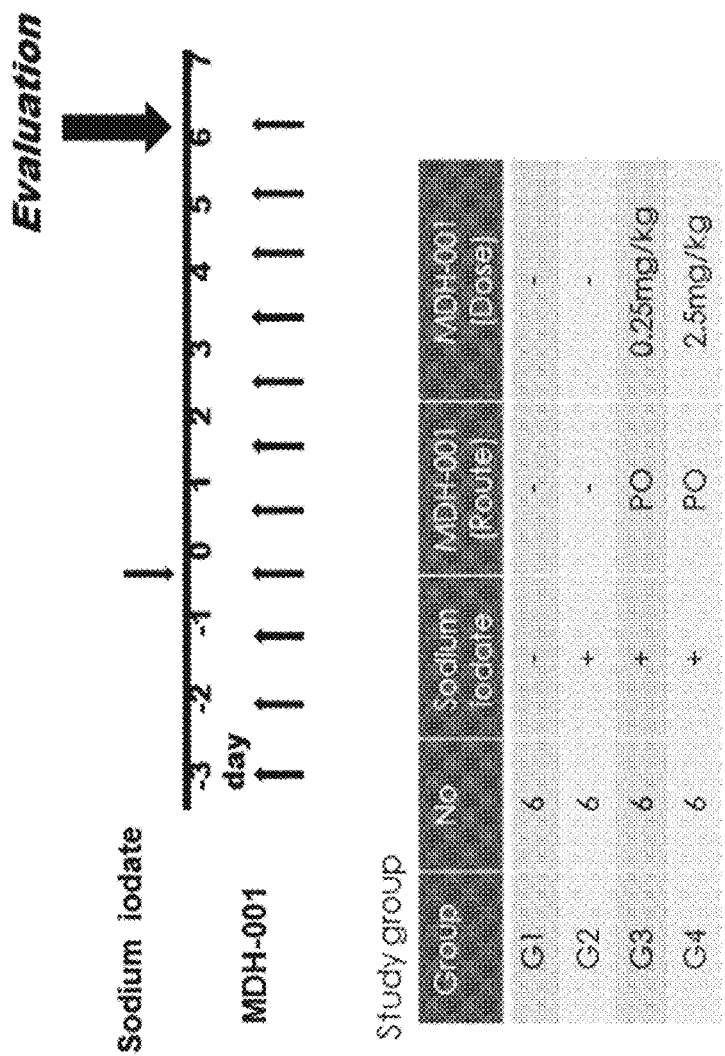
FIG. 5 shows an animal model test and evaluation methods for confirming the efficacy on an ocular disease by oral administration of *Lactobacillus paracasei*-derived extracellular vesicles according to one embodiment of the present invention.

Therefore, to induce an ocular disease by oxidative stress, sodium iodate (SI), which is a material for inducing macular degeneration by oxidative stress, was intravenously administered into a rabbit once. To evaluate the therapeutic effect of the *Lactobacillus paracasei*-derived extracellular vesicles, 0.25 mg/kg and 2.5 mg/kg of the *Lactobacillus paracasei*-derived extracellular vesicles (MDH-001) were orally administered once daily 3 days before induction to 7 days after induction. For evaluation, a retinal degenerated area was taken with a fundus camera (TRC-50IX, TOPCON, Japan) on the final administration day, i.e., on day 7 after induction of the disease, and analyzed (FIG. 5).

Figure 6:
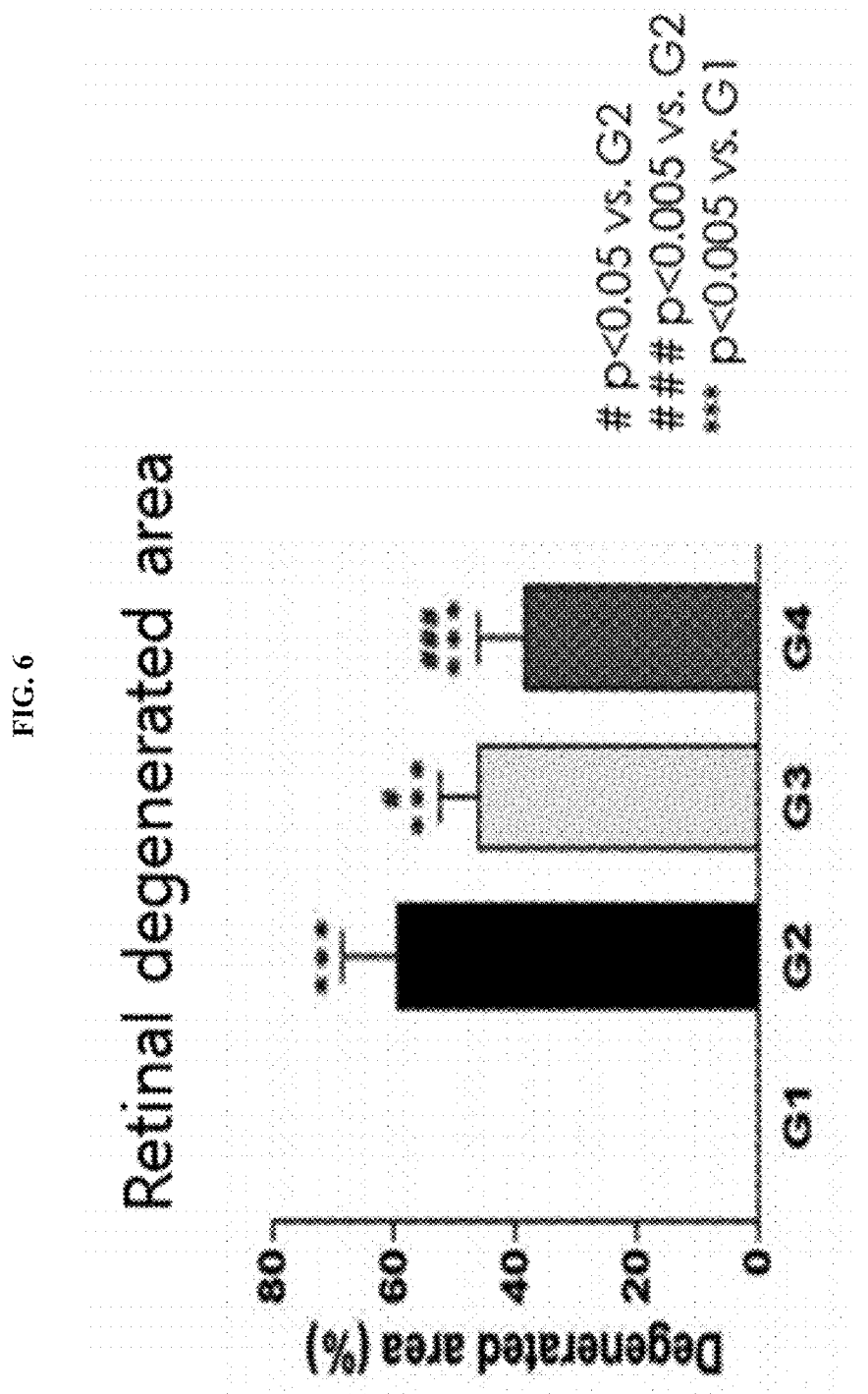
FIG. 6 is a diagram showing a result obtained by measuring a retinal degenerated area of treatment groups compared to a control by oral administration of *Lactobacillus paracasei*-derived extracellular vesicles into a rabbit model with an ocular disease in order to determine the efficacy on the ocular disease. G1: untreated negative control, G2: disease-induced positive control, G3: low dose vesicle-treated group, G4: high dose vesicle-treated group.

As a result, as shown in FIG. 6, in a low-dose vesicle (MDH-001)-treated group (G3) and a high-dose vesicle (MDH-001)-treated group (G4), compared to a positive control (G2), the degenerated area of the retinal pigment epithelium (RPE) was statistically significantly reduced, confirming dose-dependence.

Meanwhile, to evaluate the effect of the *Lactobacillus paracasei*-derived extracellular vesicles in treatment of macular degeneration, after instilling a mydriatic agent (Midriacil 1% eye drop) into the right eye of the rabbit, the animal was anesthetized, and then its fundus was photographed with a fundus camera. The result is shown in FIG. 7.

Figure 7:
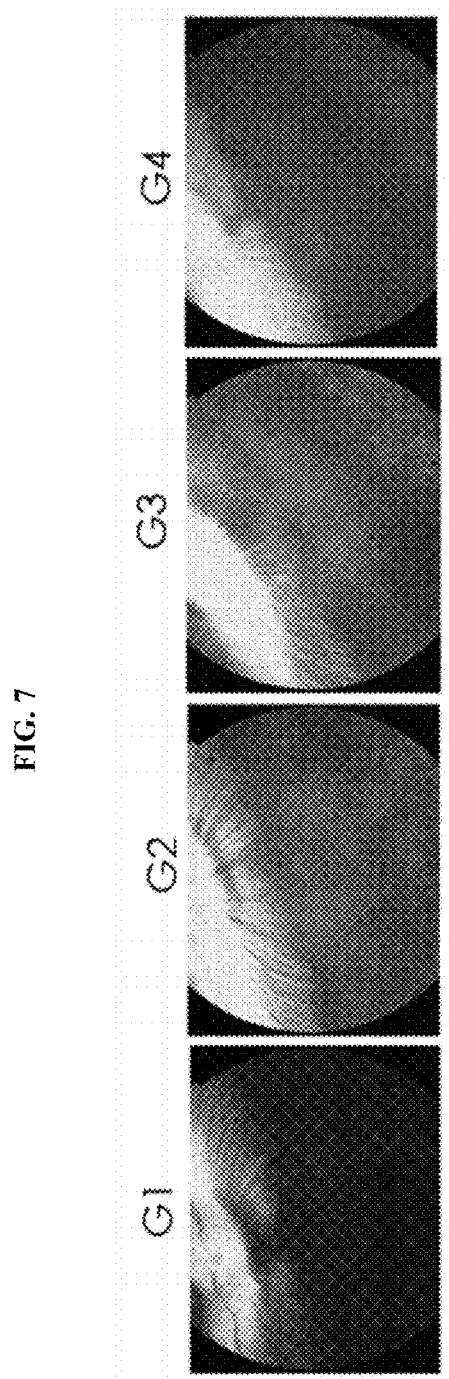
FIG. 7 is a set of photographs of the fundus taken with a fundus camera (TRC-50IX, TOPCON, Japan) after oral administration of *Lactobacillus paracasei*-derived extracellular vesicles into a rabbit model with an ocular disease caused by oxidative stress in order to determine the efficacy on an age-related ocular disease. G1: untreated negative control, G2: disease-induced positive control, G3: low dose vesicle-treated group, G4: high dose vesicle-treated group.

As shown in FIG. 7, it was seen that almost no macular degeneration was shown in a negative control (G1), and macular degeneration was clearly shown in a positive control (G2) in which the disease was induced. In addition, it can be seen that, in the low-dose vesicle-treated group (G3) and the high-dose vesicle-treated group (G4), compared to the positive control, macular degeneration was significantly reduced, and in the high-dose treated group, a reduction effect was more clearly shown.

Figure 8:
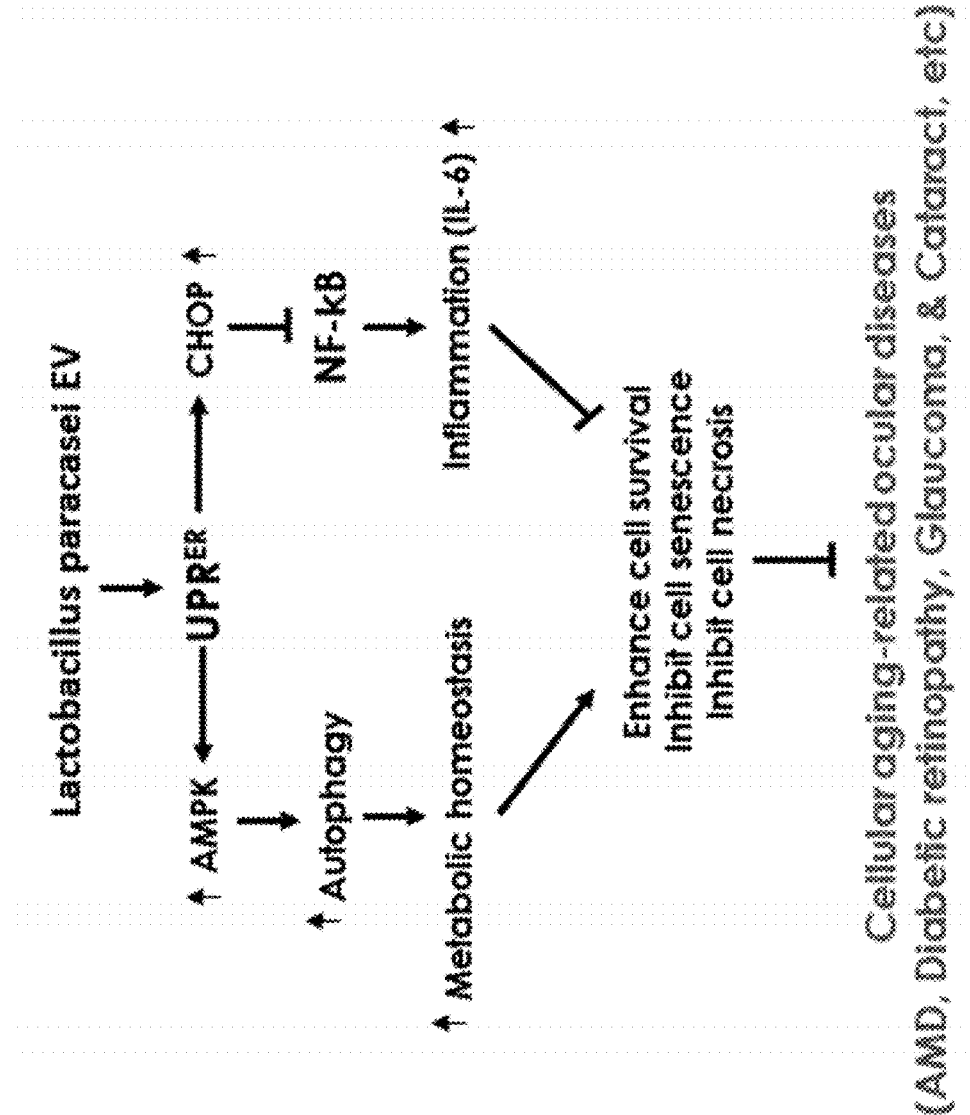
FIG. 8 is a diagram illustrating an action mechanism of *Lactobacillus paracasei*-derived extracellular vesicles for an ocular disease according to one embodiment of the present invention.

From the above results, it was seen that the *Lactobacillus paracasei*-derived extracellular vesicles of the present invention can effectively inhibit the occurrence of an ocular disease by oxidative stress. Particularly, it was confirmed that causes of cell age-related ocular diseases can be efficiently regulated by not only inhibiting the secretion of an inflammatory mediator by a pathogenic factor but also increasing the resistance to metabolic stress through AMPK signaling (FIG. 8).

Therefore, it is expected that the *Lactobacillus paracasei*-derived extracellular vesicles of the present invention can be used for alleviating, preventing or treating age-related and inflammatory ocular diseases.

The above-described description of the present invention is provided for illustrative purposes, and those of ordinary skill in the art to which the present invention pertains will understand that the present invention can be easily modified into other specific forms without changing the technical spirit or essential features of the present invention. Therefore, it should be understood that the above-described Examples are illustrative only in all aspects and are not restrictive.

INDUSTRIAL APPLICABILITY

It was confirmed that, after being absorbed into the body, *Lactobacillus paracasei*-derived extracellular vesicles according to the present invention are distributed in the central nervous system through the blood brain barrier (BBB), after being absorbed into cells, effectively inhibit the secretion of IL-6, which is the main mediator of intractable inflammatory diseases, activate AMPK signaling to increase metabolic function, and efficiently inhibit the occurrence of an ocular disease caused by cell senescence and inflammation. Further, as it was confirmed that, when the vesicles were administered into a rabbit model with an ocular disease caused by oxidative stress, the occurrence of retinal degeneration caused by oxidative stress was significantly inhibited, the *Lactobacillus paracasei*-derived extracellular vesicles according to the present invention are able to be widely used as a drug for alleviating, preventing or treating an ocular disease, and thus has industrial applicability.

The invention claimed is:

1. A method of alleviating or treating an ocular disease comprising administering to a subject in need thereof a composition comprising vesicles derived from *Lactobacillus paracasei* as an active ingredient.

2. The method of claim 1, wherein the ocular disease is age-related ocular disease.

3. The method of claim 1, wherein the ocular disease is inflammatory ocular disease.

4. The method of claim 1, wherein the ocular disease is one or more diseases selected from the group consisting of Leber congenital amaurosis (LCA), Stargardt's disease, Usher syndrome, choroidal insufficiency, Rod-Cone or Cone-Rod dystrophy, ciliopathy, a mitochondrial disorder, progressive retinal atrophy, a degenerative retinal disease, age-related macular degeneration (AMD), wet AMD, dry AMD, map atrophy, familial or acquired maculopathy, a retinal photoreceptor disease, a retinal pigment epithelium-related disease, diabetic retinopathy, cystic macular edema, retinal detachment, traumatic retinal damage, iatrogenic retinal damage, a macular hole, macular telangiectasia, a ganglion cell disease, an optic nerve cell disease, glaucoma, a cataract, optic neuropathy, ischemic retinal disease, retinopathy of prematurity, retinal vessel occlusion, familial macroaneurism, a retinal vascular disease, an ophthalmic vascular disease, retinal nerve cell degeneration caused by glaucoma and ischemic optic neuropathy.

5. The method of claim 3, wherein the inflammatory ocular disease is one or more diseases selected from the group consisting of retinitis pigmentosa (RP), conjunctivitis, scleritis, keratitis, iritis, uveitis, chorioretinitis, choroiditis, and retinitis.

6. The method of claim 1, wherein the vesicles have an average diameter of 10 to 300 nm.

7. The method of claim 1, wherein the vesicles are naturally or artificially secreted from *Lactobacillus paracasei*.

8. The method of claim 1, wherein the vesicles are isolated from a *Lactobacillus paracasei* culture solution or a food prepared by adding *Lactobacillus paracasei*.

9. The method of claim 1, wherein the composition is a pharmaceutical composition.

10. The method of claim 1, wherein the composition is a food composition.

11. The method of claim 1, wherein the composition is a quasi-drug composition.

12. The method of claim 1, wherein the composition is an inhalable composition.

13. A method for delivery of drug for treating an ocular disease, the method comprising administering a composition comprising vesicles derived from *Lactobacillus paracasei* to a subject in need thereof.

* * * * *